United States Patent
Durand et al.

(10) Patent No.: US 6,237,396 B1
(45) Date of Patent: May 29, 2001

(54) INTEGRATED ANALYSIS PROCESS AND DEVICE FOR HYDROCARBON CHARACTERIZATION BY DISTILLATION SIMULATION

(75) Inventors: Jean-Pierre Durand, La Celle Saint Cloud; Eric Robert, Rueil-Malmaison; Véronique Ruffier-Meray, Poissy, all of (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 09/468,335

(22) Filed: Dec. 21, 1999

(30) Foreign Application Priority Data

Dec. 22, 1998 (FR) .................................................. 98 16298

(51) Int. Cl.$^7$ ............................. G01N 30/02; B01D 15/08
(52) U.S. Cl. ...................... 73/23.35; 73/23.37; 73/23.4; 73/61.52; 436/161; 210/656; 95/82; 95/86
(58) Field of Search ............................... 73/19.02, 23.35, 73/23.37, 23.38, 23.4, 23.42, 61.52, 61.55, 61.56; 210/656; 436/161; 95/82, 86

(56) References Cited

U.S. PATENT DOCUMENTS

| | | |
|---|---|---|
| 4,204,952 | 5/1980 | Snyder ..................................... 95/86 |
| 4,757,023 | 7/1988 | Trestianu . |
| 4,786,475 | 11/1988 | Trestianu et al. ....................... 422/89 |
| 4,935,145 | 6/1990 | Cortes et al. ......................... 210/656 |
| 4,971,915 | 11/1990 | Schwartz . |
| 5,127,957 | 7/1992 | Heikkila et al. ...................... 210/656 |
| 5,242,471 | 9/1993 | Markham et al. ..................... 73/23.4 |
| 5,322,627 | 6/1994 | Berger et al. ......................... 210/656 |
| 5,808,180 | 9/1998 | Roussis et al. ...................... 73/23.35 |

OTHER PUBLICATIONS

Durand JP, Analusis (Dec. 1995), 23(10), p. 481–3.
JP Durant et al Simulated Distillation Methods For Petroleum Fractions With Minimal Residue In the Boiling Range Of 35–700 Degrees' Journal of Chromatographic Science, vol. 36, No. 9, Sep. 1998 pp. 431–434.

Primary Examiner—Hezron Williams
Assistant Examiner—Michael Cygan
(74) Attorney, Agent, or Firm—Antonelli, Terry, Stout & Kraus, LLP

(57) ABSTRACT

Integrated analysis process and device for characterization of hydrocarbons in a petroleum product, in distillation fractions, by simulated distillation. The hydrocarbons of a petroleum sample are characterized without fractional distillation by coupling gas chromatography (GC) with liquid chromatography (LC) techniques. GC simulated distillation (SD) is carried out. The separation column is preceded by a precolumn of the same nature but shorter. At the outlet of the main column, retention means (CT, AC) allow to collect and to store one or more light fractions that are sent each to a GC analytical column (6) allowing detailed analysis of the hydrocarbons, and one or more middle fractions. The remaining heavy fraction is collected at the precolumn outlet. The middle and heavy fractions are characterized by a combined LC-GC chromatography unit. Several interfaces allowing GC-GC-LC-GC coupling are described. The process and device can be applied for characterization of reservoir fluids or of refining process effluents for example.

8 Claims, 2 Drawing Sheets

INTEGRATED ANALYSIS PROCESS AND DEVICE FOR HYDROCARBON CHARACTERIZATION BY DISTILLATION SIMULATION

FIELD OF THE INVENTION

The present invention relates to an integrated analytical process for characterization of hydrocarbons in a petroleum product, in distillation fractions, by simulated distillation.

The process according to the invention can be used in many fields, notably for characterization of reservoir fluids or of petrochemical refining products.

BACKGROUND OF THE INVENTION

No analytical technique currently allows to directly characterize a petroleum product having a wide boiling range. Fractional distillation is necessary in order to apply to each fraction standard analytical methods or methods described in the literature. This procedure is very long and expensive, and it can lead to errors.

Considerable work and many publications deal with GC simulated distillation, GC-GC and GC-LC couplings and associated characterization methods. Examples thereof are:

Simulated distillation:
ASTM D 5307—1992; <<Determination of Boiling Range Distribution of Crude Petroleum by Gas Chromatography>>, American Society for Testing and Materials;
J. P. Durand, et al : <<Simulated Distillation Methods for Petroleum Fractions with Minimal Residue in the Boiling range of 35–700° C.>>, J. of Chromatographic Science, Vol.36, September 1998.

Couplings:
There are standard detailed analysis methods for the light fraction.
ASTM D 5134—1990, <<Detailed Analysis of Petroleum Naphthas Through n-Nonane by Capillary Gas Chromatography>>, American Society for Testing and Materials;
NF07-086, <<Détermination des teneurs en familles chimiques d'hydrocarbures dans les essences pour moteurs automobiles à partir de l'analyse détaillée>>, Association Française de normalisation, Paris La Défense, Cédex.

The use of GC-GC coupling only for analysis of the light fraction without distillation of the sample with these methods is also described by:
J. P. Durand et al: <<Direct and Automatic Capillary GC Analysis for Molecular Weight Determination and Distribution, in Crude Oils and Condensates up to C20>>, J. High Resolut. Chromatogr., 12, 1989, 230–234;
J. P. Durand et al: <<Detailed Characterization of Petroleum Products with Capillary GC analyzers>>, Analysis, 1995, 23, 481–483.

There are also many publications on LC-GC coupling. The interfaces allowing on-line coupling between LC and GC are described by K. Grob in <<On-line coupled LC-GC>>, Hüthig Ed., 1991.

As for characterization of middle and heavy fractions, the following examples can be cited:
G. W. Kelly et al: <<The use of combined LC-GC for the analysis of fuel products: a review>>, JHRC, Vol.17, 1994, 390–397;
A. Trisciani et al: <<Characterization of fuel samples by on-line LC-GC with automatic group-type separation of hydrocarbons>>, JHRC, Vol.17, 1994, 452–456;
K. J. Welch et al: <<Analysis of fossil fuel fractions by on-line coupled microcolumn HPLC-capillary GC-MS>>, HRC, 15, 1992, 171–175;
C. Ostman et al: <<On-line liquid chromatography-gas chromatography for automated clean-up and analysis of polycyclic aromatic hydrocarbons>>, HRC, 15, 1992, 437–443.

SUMMARY OF THE INVENTION

The integrated analysis process for characterization of a hydrocarbon sample in distillation fractions according to the invention is characterized in that simulated distillation by gas chromatography is carried out with a layout of two interconnected columns, so as to separate the sample into at least a first light fraction and at least another, heavier fraction, said fractions are collected after separation on retention means, each light fraction on the one hand and each of the heavier fractions on the other hand is analysed in detail by connecting up the corresponding retention means respectively with one or more gas chromatography units and with a combined liquid and gas chromatography unit.

The integrated analysis system for implementing the process comprises:
a first gas chromatography device laid-out to perform separation of the sample into at least a first light fraction and at least another, heavier fraction,
retention means for collecting said fractions after separation,
one or more gas chromatography columns for detailed analysis of each light fraction, by connecting up the corresponding retention means, and
a combined liquid and gas chromatography unit for analysing each one of the heavier fractions by connecting up and flushing of the corresponding retention means.

According to an embodiment, the first gas chromatography device comprises a capillary precolumn and a capillary column connected in series, a first multiway valve for connecting the outlet of the precolumn to a first retention means for the heavier phase, and a second multiway valve cooperating with the first valve and a source of gaseous fluid under pressure for selectively displacing at least a second, lighter phase out of the capillary column into at least a second retention means for this second phase (two for example, one for a light fraction and at least another one for a middle fraction).

The combined liquid and gas chromatography unit comprises for example a liquid chromatography column, a series of valves for intermittently connecting a retention means intended for a heavier fraction with solvent pumping means, with a liquid chromatography column and a gas chromatography unit, by means of a LC/GC type interface.

According to an embodiment, the series of valves comprises a first valve suited, in a first position, to communicate the pumping means with the liquid chromatography column and, simultaneously, a retention means with a solvent injection means, and, in a second position, to connect in series, by means of a second valve, the pumping means, the retention means, said liquid chromatography column and gas chromatography unit (GC).

According to an embodiment, gas chromatography unit (GC) comprises for example a retention-gap column for evaporation of the solvent, an analytical precolumn, evaporation and discharge means arranged on either side of this precolumn for solvent removal, and an analytical column associated with a FID detector.

An ultraviolet detector can be used for detection of the fractions transferred to said chromatography unit.

The analysis process according to the invention is advantageous because it allows, from a sample taken under pressure, without previous expansion, via a pressure injection valve, to obtain better characterization of fluids, notably of the heavy fraction of condensate gases (HT/HT fluids), which is essential for accurate calculation of their thermodynamic behaviour. It allows to obtain very complete analytical characterization of fluids, with a considerable saving in time in relation to conventional fractional distillation methods, and therefore with cost reduction. Furthermore, this result can be obtained with reduced samples, entirely compatible with the relatively small quantities that are generally available during preliminary reservoir effluent surveys.

BRIEF DESCRIPTION OF THE DRAWINGS

Other features and advantages of the process according to the invention will be clear from reading the description hereafter, with reference to the accompanying drawings wherein.

DETAILED DESCRIPTION OF THE INVENTION

In a context of reduction and integration of complex analytical procedures such as those allowing characterization of petroleum products, the samples analysed by means of the method according to the invention are reservoir fluids or refining process effluents comprising both light and heavy hydrocarbons. The number of carbon atoms of the hydrocarbons can range from 1 to 100. First the simulated distillation layout allowing prefractionation of the samples into light fraction(s), middle fraction(s) and a heavy fraction, then the chromatographic analysis of these fractions will be described.

1) Distillation simulation part

Figure 1:
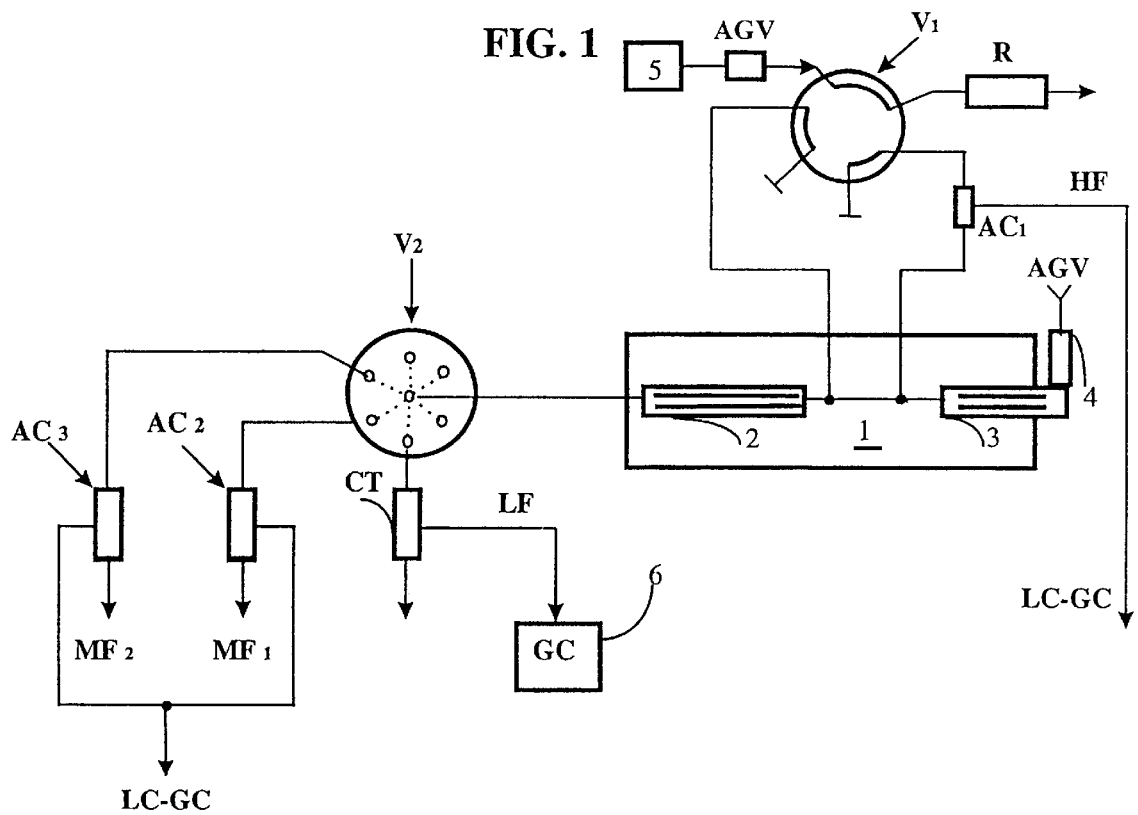
FIG. 1 diagrammatically shows the analytical layout of the distillation simulation part where the valves are positioned for injection of the sample, FIG. 2 diagrammatically shows the analytical layout of the distillation simulation part where the valves are positioned for collection of the heavy fraction and of the middle fraction(s), FIG. 3 diagrammatically shows the layout allowing liquid chromatography-gas chromatography (LC-GC) coupling, FIG. 4 diagrammatically shows a first configuration of injection valve V3 in the layout of FIG. 3, and FIG. 5 diagrammatically shows another configuration of valves V3 and V4 of the same layout of FIG. 3, allowing injection of the middle and heavy fractions of the trapped sample into the LC/GC chromatography column.
Figure 2:
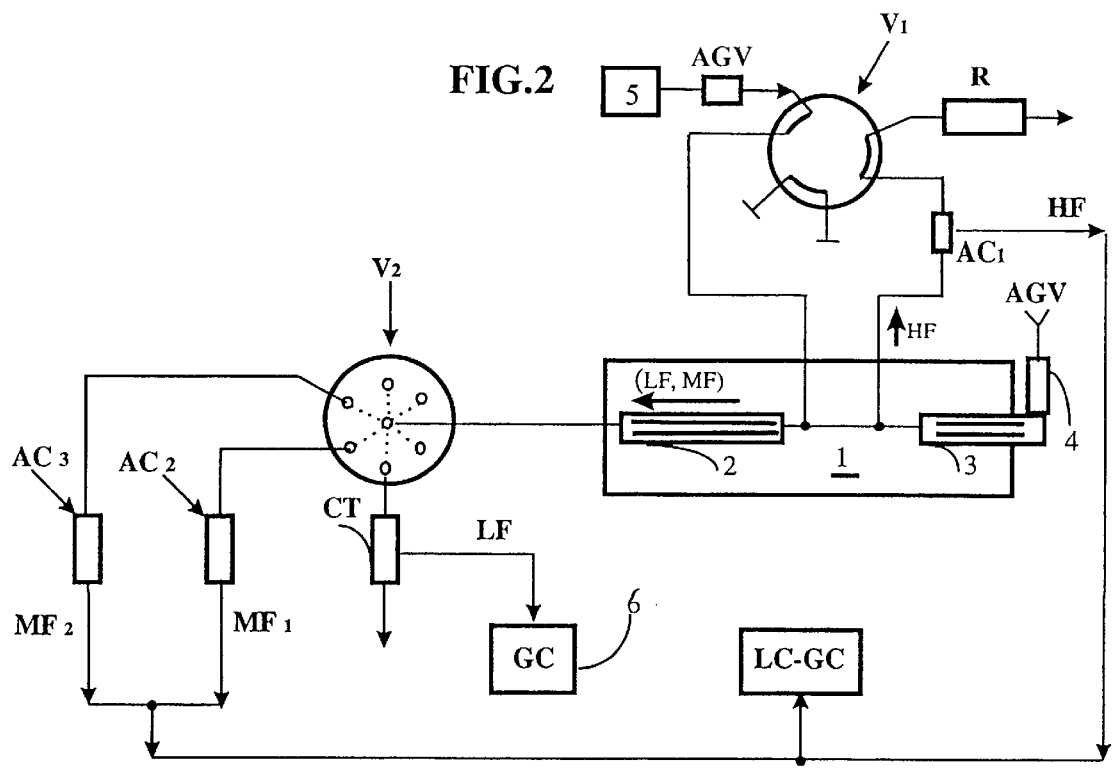

In FIGS. 1, 2, the following symbols denote respectively:
AC1–AC3, low retention power adsorbent cartridges,
CT, a cold trap,
R, a restrictor establishing a pressure drop,
AGV, injection of an auxiliary carrier gas,
LF, MF1, MF2, the light fraction and middle fractions 1 and 2 respectively,
LC and GC, liquid and gas chromatography systems respectively.

The method is implemented by means of a simulated distillation device allowing prefractionation of the sample, which comprises (FIGS. 1, 2) in a single still 1:
a simulated distillation capillary column 2, 0.53 mm in inside diameter, with a nonpolar stationary phase film; the length and the thickness of the film are optimized to secure elution of the C50 normal paraffin and to obtain a resolution higher than 3 between the C5 and C6 normal paraffins,
a capillary precolumn 3, 0.52 mm in inside diameter, with a nonpolar stationary phase film; the length and the thickness of the film are optimized to secure elution of the C100 normal paraffin.

An injector 4 of a well-known type, referred to as on-column injector, possibly allows, via a pressure injection valve, injection of the sample into precolumn 3, carried along by a carrier gas stream.

A multiway switching valve V1 using the known back-pressure technique is installed between precolumn 3 and simulated distillation column 2. A second multiway selection valve V2 is installed at the outlet of simulated distillation column 2.

In the position illustrated in FIG. 1, valve V1 ensures series operation of column 2 and precolumn 3. In the position shown in FIG. 2, the heavy fraction HF ($C_{30+}$ for example) is collected from precolumn 3 onto adsorbent cartridge AC1. This valve V1 is simultaneously positioned to lead an auxiliary gas stream AGV coming from a source 5 towards simulated distillation column 2 so as to transfer the middle fractions ($C_{15+}$–$C_{30}$ for example) on the one hand and one or more light fractions ($C_{15-}$ for example) on the other hand respectively onto adsorbent cartridges AC2 and into trap(s) CT, by means of selection valve V2. In fact, there may be several light fractions in case of pressure injections, in which case each one of them is collected separately in different cold traps.

Each cold trap CT consists for example of a capillary 0.50 mm in inside diameter, with a nonpolar stationary phase film; the length, the thickness of the film and the trapping temperature are optimized to secure trapping of the lighter constituents.

Each fraction retained in a cold trap CT is analysed in a specific gas chromatograph 6.

2) LC/GC coupling part

Figure 3:
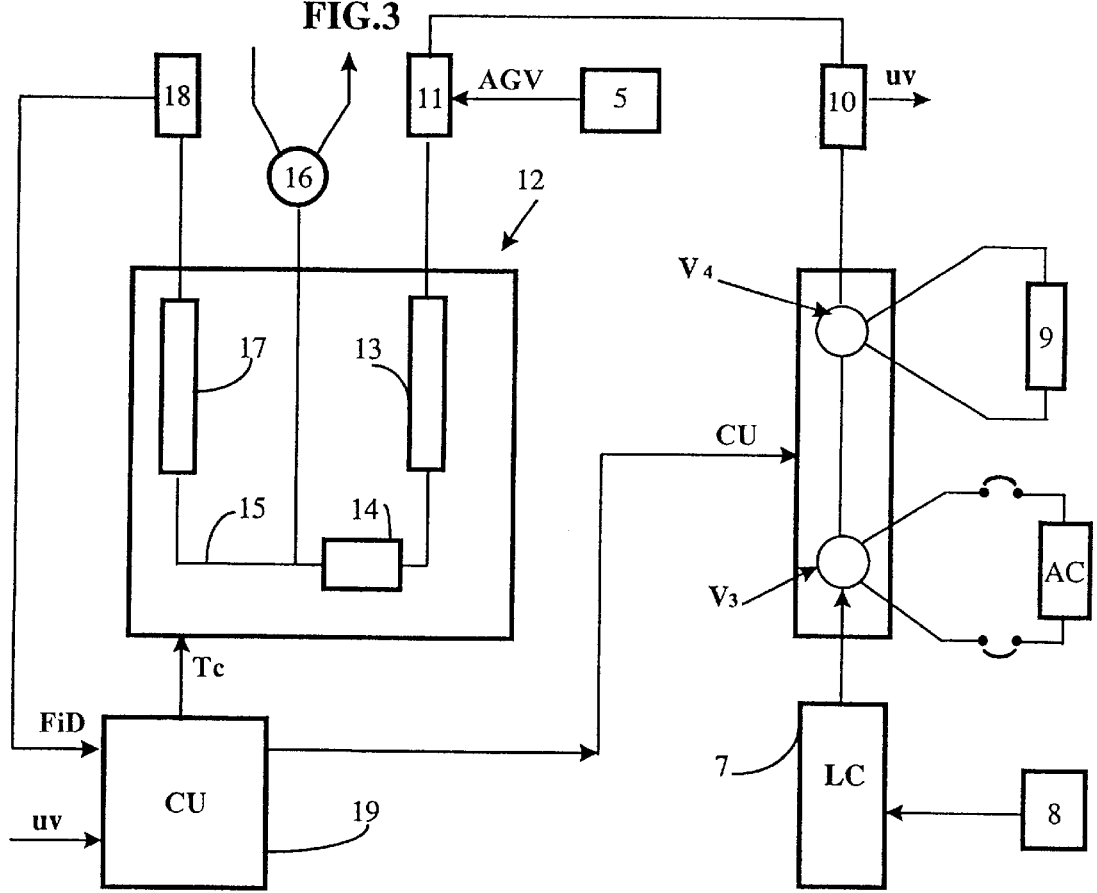

In order to carry out the following liquid and gas (LC, GC) chromatography operations on the fractions isolated with the layout shown in FIGS. 1, 2, a well-known LC/GC system selected from those described in the literature, such as the Dualchrom 3000™ for example, can be used. The configuration of the LC/GC system is diagrammatically shown in FIG. 3 and detailed hereafter:

a) LC part

It comprises a syringe type pump 7 for example, connected on the one hand to a tank 8 containing an elution solvent and, on the other hand, to a multiway injection valve V3. A second pump (not shown), referred to as slave pump, can also be used to apply an elution gradient. Adsorbent cartridges AC or cold trap CT can be connected to two ways of injection valve V3. A multiway valve V4, referred to as retro-elution or back-flush valve, is connected to a liquid chromatography (LC) column 9, to valve V3 and to the inlet of an ultraviolet detector 10 for control of the transferred fractions during transfer to a LC/GC interface module 11 of a known type, provided with an inlet for a gas stream AGV, described for example by K. Grob mentioned above.

At the outlet of LC/GC interface module 11, the fraction is transferred to a gas chromatography (GC) unit 12 comprising a retention-gap column 13 in which the most part of the solvent is evaporated. This column 13 is connected to an analytical precolumn 14. At the outlet thereof, a tee 15 comprises a first way allowing discharge of the solvent fumes into a leak-by 16 during the transfer stage and another way for leading the solutes to be analysed to a GC analytical column 17 at the end of the transfer stage. This column 17 communicates with a FID type detector 18 for example, conventionally used in chromatography.

The transfer mode used in the LC/GC coupling can be either injection loop type transfer, which consists in trapping a fraction coming from column 9 before it is transferred to gas chromatography column 13, or direct transfer (on-column) of this fraction into column 13.

Analytical column 17 is a simulated distillation capillary column, 0.52 mm in inside diameter for example, with a nonpolar stationary phase film; the length and the thickness of the film are optimized to secure elution of the C100 normal paraffin. Analytical precolumn 14, whatever the interface type, is a column of the same nature as analytical column 17, which is for example 0.50 mm in inside diameter and 2 to 5 m long.

Optimization of retention gap column 13 and of the transfer conditions, notably the temperature, depends on the type of interface used. In the case of an injection-loop LC/GC interface, a 2.5 to 7.5-m long column, 0.50 mm in inside diameter, will be used. In case of direct transfer into GC column 14, a 10 to 30-m long column, 0.50 mm in inside diameter, will be used.

A control unit CU 19 receives the signals measured by FID detector 18, as well as the signals UV measured by ultraviolet detector 10, and generates the programme controlling temperatures Tc and valves V1–V4.

Fractions collection

Light fraction(s)

At the outlet of selection valve V2 (FIGS. 1, 2), each light fraction is collected in a cryogenic trap CT. The latter is thereafter desorbed through heating at the inlet of the injector of chromatograph 6 (FIG. 1) that ensures detailed analysis of the light fraction released.

Middle and heavy fractions

Several middle fractions can be collected on possibly adsorbent cartridges AC2, AC3 or in a cold trap CT at the outlet of selection valve V2. The heavy fraction is also collected on adsorbent cartridge AC1 (or possibly in a cold trap) by means of switching valve V1.

In the case of cartridges AC, the filling material must be sufficiently adsorbent to trap all of the constituents of the middle fractions and of the heavy fraction, but it must allow desorption of all these fractions by elution with an apolar solvent, pentane for example, or with a weakly polar solvent such as pentane-dichloromethane mixtures for example. These cartridges can be filled with commonly available known supports such as glass microballoons, network polymer balls, styrene-divinylbenzene for example, or with grafted supports for liquid chromatography such as alkyl grafted phases (preferably C1 or C4 to prevent too high retention of the alkyl aliphatic and aromatic hydrocarbons) or amino or cyano grafted phases.

For cold traps CT, a capillary 0.50 mm in inside diameter, comprising or not a nonpolar stationary phase film such as polydimethylsiloxane, is preferably used. The length, the thickness of the film and the trapping temperature are optimized to secure trapping of all the constituents.

Figure 4:
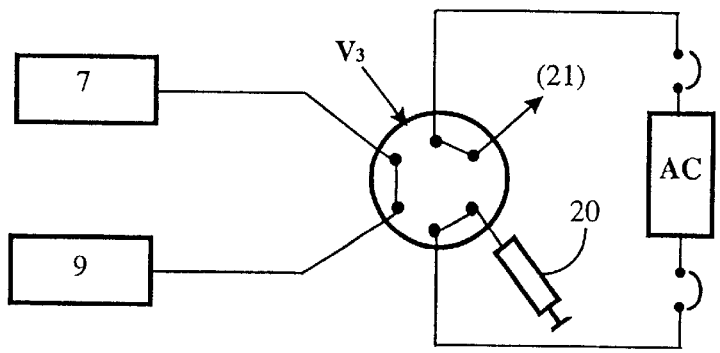
Figure 5:
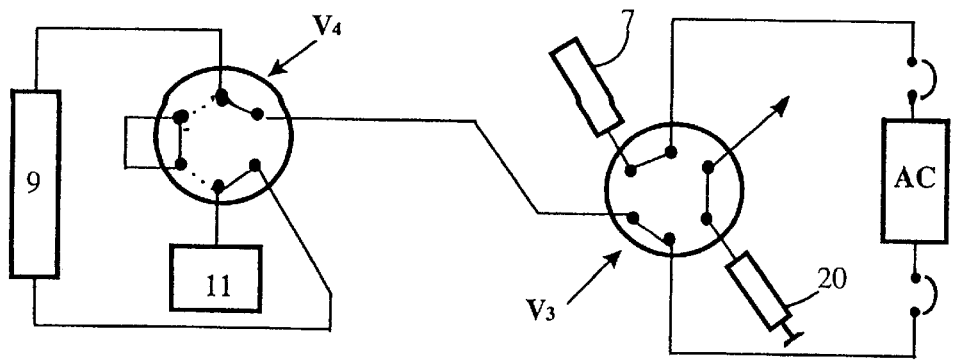

These cartridges or traps can be either connected in line on the LC/GC system (FIG. 3), or transferred near the injection valve V3 thereof after trapping of the fractions. FIG. 4 shows the connection diagram of a cartridge AC or of a trap CT on injection valve V3 of the LC/GC system. Valve V3 is so positioned that pump 4 is connected to LC column 9 by means of valve V4. Furthermore, since trapping of the fraction occurs in the gas phase and changing to the liquid phase is required for LC/GC analysis, the position of valve V3 allows injection of a solvent by means of a syringe 20 for example, in order to flush the retention means (the cartridge or the connected trap) and to draw away the gases into a drain 21 so as to fill it, as well as the connection lines. The position of valves V3, V4 shown in FIG. 5 allows to perform retro-elution or back-flushing of the LC column to elute the most polar constituents of the fractions.

Within the scope of the present process, injection-loop transfer is preferably used as it is easier to implement. This transfer mode allows quantitative transfer of the hydrocarbons having a number of carbon atoms above 12 if the elution solvent is pentane.

Embodiments where the middle fractions and the heavy fraction are retained in adsorbent cartridges have been described. If need be, these cartridges can however be replaced by retention-gap cold traps without departing from the scope of the invention.

What is claimed is:

1. An integrated analysis process for characterizing a hydrocarbon sample in distillation fractions, characterized in that it comprises:

carrying out simulated distillation by gas chromatography in a layout of two interconnected columns, so as to separate the sample into at least a first light fraction and at least another, heavier fraction, collecting said fractions after separation on retention means (AC, CT), analysing in detail each light fraction on the one hand and each heavier fraction on the other hand by connecting up the corresponding retention means (AC, CT) respectively with at least one gas chromatography unit (6) and with a combined liquid and gas chromatography unit (LC-GC).

2. An integrated analysis system for characterizing a hydrocarbon sample in distillation fractions, characterized in that it comprises:

a first gas chromatography device (1) laid-out for separation of the sample into at least a first light fraction and at least another, heavier fraction, retention means (AC, CT) for collecting said fractions after separation, at least one gas chromatography column (6) for detailed analysis of each light fraction by connecting up the corresponding retention means (CT), and a combined liquid and gas chromatography unit (LC-GC) for analysing each heavier fraction by connecting up and flushing the corresponding retention means.

3. A system as claimed in claim 2, characterized in that the first gas chromatography device comprises a capillary precolumn (3) and a capillary column (2) connected in series, a first multiway valve (V1) for connecting the outlet of precolumn (3) to a first retention means (AC1) for the heavier phase, and a second multiway valve (V2) cooperating with first valve (V1) and a source (5) of gaseous fluid under pressure for selective displacement of at least a second lighter phase out of capillary column (2) into at least a second retention means (CT, AC2, AC3) for this second phase.

4. A system as claimed in claim 3, characterized in that the combined liquid and gas chromatography unit comprises a liquid chromatography (LC) column (9), a series of valves (V3, V4) for intermittently connecting a retention means (AC) for a heavier fraction with solvent pumping means (7, 8), with a liquid chromatography column (9) and a gas chromatography unit (12), by means of a LC/GC type interface (11).

5. A system as claimed in claim 4, characterized in that the series of valves comprises a first valve (V3) suited, in a first position, to communicate pumping means (7, 8) with liquid chromatography column (9) and, simultaneously, a retention means (AC) with a solvent injection means (20) and, in a second position, to connect in series, by means of a second valve (V4), pumping means (7, 8), retention means (AC, CT) of said chromatography column (9) and gas chromatography (GC) unit (12).

6. A system as claimed in claim 4, characterized in that said gas chromatography (GC) unit (12) comprises a retention-gap column (13) for evaporation of the solvent, an analytical (GC) precolumn (14), evaporation and discharge means (13, 15, 16) arranged on either side of this precolumn (14) for solvent removal, and an analytical column (17) associated with a FID detector (18).

7. A system as claimed in claim 4, characterized in that it comprises an ultraviolet detector for detecting the fractions transferred into said chromatography unit (12).

8. A system as claimed in claim 2, characterized in that it comprises retention means connected to second valve (V2), suited to retain at least one light fraction (LF) and at least one middle fraction (MF).

* * * * *